(12) United States Patent
Norman

(10) Patent No.: US 7,736,635 B2
(45) Date of Patent: Jun. 15, 2010

(54) BRANCHED MOLECULAR SCAFFOLDS FOR LINKING POLYMER RESIDUES TO BIOLOGICALLY ACTIVE MOIETIES

(75) Inventor: Timothy John Norman, Great Missenden (GB)

(73) Assignee: UCB Pharma S.A., Brussels (BE)

( * ) Notice: Subject to any disclaimer, the term of this patent is extended or adjusted under 35 U.S.C. 154(b) by 81 days.

(21) Appl. No.: 10/583,642

(22) PCT Filed: Dec. 14, 2004

(86) PCT No.: PCT/GB2004/005246

§ 371 (c)(1),
(2), (4) Date: Jun. 20, 2006

(87) PCT Pub. No.: WO2005/061005

PCT Pub. Date: Jul. 7, 2005

(65) Prior Publication Data

US 2007/0128150 A1 Jun. 7, 2007

(30) Foreign Application Priority Data

Dec. 23, 2003 (GB) .................................. 0329825.4

(51) Int. Cl.
*A61K 31/74* (2006.01)
(52) U.S. Cl. .................................................. 424/78.17
(58) Field of Classification Search ........................ None
See application file for complete search history.

(56) References Cited

U.S. PATENT DOCUMENTS

| | | | |
|---|---|---|---|
| 4,946,778 A | 8/1990 | Ladner et al. | 435/69.6 |
| 5,219,996 A | 6/1993 | Bodner et al. | 530/387.3 |
| 5,223,409 A | 6/1993 | Ladner et al. | 435/69.7 |
| 5,403,484 A | 4/1995 | Ladner et al. | 435/235.1 |
| 5,427,908 A | 6/1995 | Dower et al. | 435/5 |
| 5,516,637 A | 5/1996 | Huang et al. | 435/6 |
| 5,571,698 A | 11/1996 | Ladner et al. | 435/69.7 |
| 5,580,717 A | 12/1996 | Dower et al. | 435/5 |
| 5,585,089 A | 12/1996 | Queen et al. | 424/133.1 |
| 5,658,727 A | 8/1997 | Barbas et al. | 435/6 |
| 5,677,425 A | 10/1997 | Bodmer et al. | 530/387.1 |
| 5,698,426 A | 12/1997 | Huse | 435/172.3 |
| 5,733,743 A | 3/1998 | Johnson et al. | 435/69.1 |
| 5,750,753 A | 5/1998 | Kimae et al. | 556/440 |
| 5,780,225 A | 7/1998 | Wigler et al. | 435/6 |
| 5,821,047 A | 10/1998 | Garrard et al. | 435/5 |
| 5,932,462 A | 8/1999 | Harris et al. | 435/188 |
| 5,969,108 A | 10/1999 | McCafferty et al. | 530/387.3 |
| 6,251,382 B1 | 6/2001 | Greenwald et al. | 424/78.17 |
| 6,362,254 B2 | 3/2002 | Harris et al. | 523/406 |
| 2002/0009426 A1* | 1/2002 | Greenwald et al. | 424/78.18 |
| 2003/0021790 A1 | 1/2003 | Hsei et al. | 424/178.1 |
| 2003/0211078 A1* | 11/2003 | Heavner | 424/85.1 |
| 2004/0225097 A1 | 11/2004 | Nho et al. | 526/333 |

FOREIGN PATENT DOCUMENTS

| | | |
|---|---|---|
| EP | 1 496 076 A1 | 1/2005 |
| GB | 0 315 450 | 7/1929 |
| GB | 0 315 457 | 7/1929 |
| GB | 0 319 588 | 3/1931 |
| GB | 0 329 825 | 5/1980 |
| WO | WO 90/02809 A1 | 3/1990 |
| WO | WO 91/10737 A1 | 7/1991 |
| WO | WO 92/01047 A1 | 1/1992 |
| WO | WO 92/02551 A1 | 2/1992 |
| WO | WO 92/18619 A1 | 10/1992 |
| WO | WO 92/22853 A1 | 12/1992 |
| WO | WO 93/08829 A1 | 5/1993 |
| WO | WO 93/11236 A1 | 6/1993 |
| WO | WO 95/15982 A2 | 6/1995 |
| WO | WO 95/20401 A1 | 8/1995 |
| WO | WO 98/25971 A1 | 6/1998 |
| WO | WO 02/27315 A3 | 4/2002 |
| WO | WO 03/31475 A3 | 4/2003 |
| WO | WO 2004060965 A2 * | 7/2004 |
| WO | WO2005/002870 A1 | 1/2005 |
| WO | WO2005/002871 A1 | 1/2005 |
| WO | WO2005/003169 A3 | 1/2005 |
| WO | WO2005/061005 A2 | 7/2005 |

OTHER PUBLICATIONS

Normaln et al, Improved Tumour Targeting with Recombinant Antibody-Macrocycle Conjugates, J. Chem. Soc., Chem. Commun., 1995, 1877-1878.*

Ames, R.S., et al., "Conversion of murine Fabs isolated from a combinatorial phage display library to full length immunoglobulins," J. Immunol. Methods, 1995, 184, 177-186.

(Continued)

*Primary Examiner*—Michael G Hartley
*Assistant Examiner*—Paul Dickinson
(74) *Attorney, Agent, or Firm*—McDonnell Boehnen Hulbert & Berghoff LLP

(57) ABSTRACT

Branched molecular scaffolds are provided which are capable of linking two polymer residues (derived, for example, from polyethylene glycol) to two, three or four residues derived from biologically active molecules (e.g. from whole antibodies or from functionally active fragments or derivatives thereof), the latter being attached to the scaffold by means of hydrolytically stable linkages.

6 Claims, No Drawings

OTHER PUBLICATIONS

Badcook, J., et al., "A novel strategy for generating monoclonal antibodies from single, isolated lymphocytes producing antibodies of defined specificities," Proc. Natl. Acad. Sci. USA, 1996, 93, 7843-7848.

Brinkman, U., et al., "Phage display of disulfide-stabilized Fv fragments," J. Immunol. Methods, 1995, 182, 41-50.

Burton, D.R., et al., "Human antibodies from combinatorial libraries," Advances in Immunology, 1994, 57, 191-280.

Chapman, A.P., et al., "Therapeutic antibody fragments with prolonged in vivo half-lives," Nature Biotechnology, 1999, 17(8), 780-783.

Chapman, A.P., "PEGylated antibodies and antibody fragments for improved therapy: a review,", Advanced Drug Delivery Reviews, 2002, 54, 531-545.

Cole, et al., "The EBV-hybridoma technique and its application to human lung cancer," Monoclonal Antibodies and Cancer Therapy, Alan R. Liss, Inc., 1985, 77-96.

Greenwald, R.B., et al., "Highly water soluble taxol derivatives: 7-polyethylene glycol carbamates and carbonates," J. Org. Chem., 1995, 60, 331-336.

Hurwitz, E., et al., "Inhibition of tumor growth by poly(ethylene glycol) derivatives of anti-ErbB2 antibodies," Cancer Immunology & Immunotherapy, 2000, 49(4-5), 226-234.

Kettleborough, C.A., et al., "Isolation of tumor cell-specific single-chain Fv from immunized mice using phage-antibody libraries and the re-construction of whole antibodies from these antibody fragments," Eur. J. Immunol., 1994, 24, 952-958.

Köhler, G., et al., "Continuous cultures of fused cells secreting antibody of predefined specificity," Nature, 1975, 256, 495-497.

Kozbor, D., et al., "the production of monoclonal antibodies from human lymphocytes," Immunology Today, 1983, 4, 72-79.

Mantovani, G., et al., "Design and synthesis of N-maleimido-functionalized hydrophilic polymers via copper mediated living radical polymerization: a suitable alternative to PEGylation chemistry," J. Am. Chem. Soc., 127(9), 2966-2973, 2005.

Milstein, C., et al., "Hybrid hybridomas and their use in immunohistochemistry," Nature, 1983, 305, 537-539.

Natarajan, A., et al., "Characterization of site specific ScFv PEGylation for tumor targeting pharmaceuticals," Bioconjugate Chem., 2005, 16(1), 113-121.

Persic, L., et al., :An integrated vector system for the eukaryotic expression of antibodies or their fragments after selection from phage display libraries, Gene, 1997, 187, 9-18.

Tessmar, J., et al., "The use of poly(ethylene glycol)-block-poly(lactic acid) derived copolymers for the rapid creation of biomimetic surfaces," Biomaterials, 2003, 24(24), 4475-4486.

Traunecker, A., et al., "Bispecific single chain molecules (Janusins) target cytotoxic lymphocytes on HIV infected cells," EMBO J., 1991, 10, 3655-3659.

* cited by examiner

BRANCHED MOLECULAR SCAFFOLDS FOR LINKING POLYMER RESIDUES TO BIOLOGICALLY ACTIVE MOIETIES

The present invention relates to branched molecular scaffolds which are capable of linking two polymer residues (derived, for example, from polyethylene glycol) to two, three or four residues derived from biologically active molecules. Methods for the production of such molecules, and pharmaceutical compositions containing them, are also provided.

The hydrophilic polymer polyethylene glycol (PEG) has been covalently attached to biologically active molecules for a variety of reasons, including to increase water solubility (Greenwald et al., *J. Org. Chem.*, 1995, 60, 331-336), to extend the circulating half-life and to reduce immunogenicity (Chapman, *Advanced Drug Delivery Reviews*, 2002, 54, 531-545). In general, site-specific attachment of PEG molecules is preferable to random attachment, which can adversely affect the biological activity of the molecule.

In order to attach a high enough molecular weight of PEG to the biologically active molecule, branched PEG molecules have been used in place of very high molecular weight linear polymer chains which can be difficult to prepare, as well as being expensive.

For various reasons, it is considered advantageous to attach more than one biologically active molecule to a single branched PEG scaffold. In such instances, for example, a substantial increase in potency can be observed.

Branched PEG polymers comprising a single site for the attachment of one or more biologically active molecules are described, for example, in U.S. Pat. Nos. 6,362,254 and 5,932,462.

U.S. Pat. No. 6,251,382 provides a branched scaffold comprising inter alia a multiplicity of separate sites for attachment of at least two polymer chains and at least two biologically active molecules. The molecules described therein are stated to be biodegradable, polymer-based conjugates having the following formula:

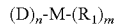

wherein
(m) and (n) independently represent positive integers, preferably from about 1 to about 6 each;
D is a residue of a biologically active moiety;
M is a multifunctional linker/spacer moiety; and
$R_1$ is a polymer residue.

The present invention provides new branched molecular scaffolds which are capable of linking two polymer residues (derived, for example, from PEG) to two, three or four residues derived from biologically active molecules, the latter being attached to the scaffold by means of hydrolytically stable linkages.

Thus, the present invention provides a compound of formula (I):

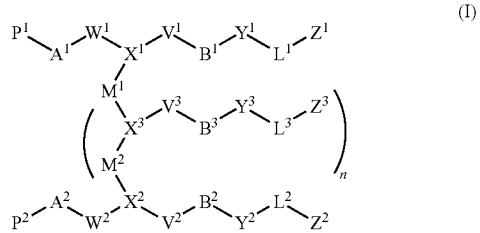

wherein
$P^1$ and $P^2$ independently represent a polymer residue;
$Z^1$, $Z^2$ and $Z^3$ independently represent the residue of a biologically active moiety;
$X^1$, $X^2$ and $X^3$ independently represent $CR^1$ or N;
$A^1$ and $A^2$ independently represent —CONH—, —NHCO—, —OC(O)N($R^2$)—, —N($R^2$)C(O)O— or —NHCONH—;
$B^1$, $B^2$ and $B^3$ independently represent —CONH— or —CO—;
$V^1$, $V^2$ and $V^3$ independently represent a covalent bond or —$(CH_2)_w$—;
$W^1$ and $W^2$ independently represent a covalent bond or —$(CH_2)_w$—;
$Y^1$, $Y^2$ and $Y^3$ independently represent —$(CH_2)_y$—;
$L^1$, $L^2$ and $L^3$ independently represent a spacer group;
$M^1$ and $M^2$ independently represent a covalent bond or —$(CH_2)_m$—;
$R^1$ represents hydrogen or $C_{1-4}$ alkyl;
$R^2$ represents hydrogen or $C_{1-4}$ alkyl;
n is zero, 1 or 2;
v is 1, 2, 3 or 4;
w is 1, 2, 3 or 4;
y is 1, 2, 3, 4, 5 or 6; and
m is 1, 2 or 3.

The present invention falls within the broadest generic scope of U.S. Pat. No. 6,251,382. However, there is no specific disclosure therein of a compound falling within the scope of formula (I) as depicted above.

As used herein, the term "$C_{1-4}$ alkyl" refers to straight-chained and branched alkyl groups containing 1 to 4 carbon atoms. Such groups are methyl, ethyl, n-propyl, isopropyl, n-butyl, isobutyl, sec-butyl and tert-butyl.

As used herein, the term "residue" will be understood to mean that portion of a polymer or of a biologically active moiety which remains after it has undergone a substitution reaction as such terminology is familiar to the person skilled in the art.

The polymer residues $P^1$ and $P^2$ in the compounds of formula (I) above will suitably be residues of substantially water-soluble, substantially non-antigenic polymers as described, for example, in U.S. Pat. No. 6,251,382 B1, with particular reference to the passage running from column 16, line 52 to column 18, line 14, the contents of which are herein incorporated by reference. Typical polymers of which $P^1$ and $P^2$ are residues include polyalkylene oxides such as polyethylene glycols (PEGs). As regards attaching PEG moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C.; and "Bioconjugation Protein Coupling Techniques for the Biomedical Sciences", 1998, M. Aslam and A. Dent, Grove Publishers, New York. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

Suitably, $P^1$ and $P^2$ are identical.

In the compounds of formula (I) above, the residues $Z^1$, $Z^2$ and $Z^3$ will suitably be residues of the entities referred to in, for example, U.S. Pat. No. 6,251,382 B1, with particular reference to the passage running from column 18, line 15 to column 22, line 67, the contents of which are herein incorporated by reference. Typical biologically active moieties of which $Z^1$, $Z^2$ and $Z^3$ are residues include antibodies and antibody fragments such as those referred to in U.S. Pat. No. 6,251,382 B1, column 22, lines 14-22.

Thus, the residues $Z^1$, $Z^2$ and $Z^3$ include whole antibodies and functionally active fragments or derivatives thereof and may be, but are not limited to, polyclonal, monoclonal, multivalent, multi-specific, humanized or chimeric antibodies, single chain antibodies, Fab fragments, Fab' and F(ab')$_2$ fragments and epitope-binding fragments of any of the above.

Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD or IgA) or subclass of immunoglobulin molecule.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, and in WO 92/02551.

Humanized antibodies are antibody molecules from non-human species having one or more complementarity determining regions (CDRs) from the non-human species and a framework region from a human immunoglobulin molecule (see, for example, U.S. Pat. No. 5,585,089).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., *Nature*, 1983, 305, 537-539; WO 93/08829; Traunecker et al., *EMBO J.*, 1991, 10, 3655-3659). Multivalent antibodies may comprise multiple specificities or may be monospecific (see, for example, WO 92/22853).

The antibodies for use in the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., Advances in Immunology, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580, 717; 5,427,908; 5,750,753; 5,821,047; 5,571,698; 5,427,908; 5,516,637; 5,780,225; 5,658,727; 5,733,743; and 5,969,108. Techniques for the production of single chain antibodies, such as those described in U.S. Pat. No. 4,946,778, can also be adapted to produce single chain antibodies. Also, transgenic mice, or other organisms, including other mammals, may be used to express humanized antibodies.

Particular antibody fragments include those described in international patent applications PCT/GB2004/002810, PCT/GB2004/002870 and PCT/GB2004/002871 (all filed on 1 Jul. 2004), claiming priority variously from United Kingdom patent applications 0315450.7, 0315457.2 (both filed on 1 Jul. 2003) and 0319588.0 (filed on 20 Aug. 2003).

Suitably, $Z^1$ and $Z^2$ are identical.

In one embodiment, $X^1$ represents $CR^1$. In another embodiment, $X^1$ represents N.

In one embodiment, $X^2$ represents $CR^1$. In another embodiment, $X^2$ represents N.

In one embodiment, $X^3$ represents $CR^1$. In another embodiment, $X^3$ represents N.

Suitably, $X^1$ and $X^2$ are identical.

Suitably, $A^1$ represents —CONH— or —NHCO—. In one embodiment, $A^1$ represents —CONH—. In another embodiment, $A^1$ represents —NHCO—.

Suitably, $A^2$ represents —CONH— or —NHCO—. In one embodiment, $A^2$ represents —CONH—. In another embodiment, A represents —NHCO—.

Suitably, $A^1$ and $A^2$ are identical.

In one embodiment, $B^1$ represents —CONH—. In another embodiment, $B^1$ represents —CO—. Where $B^1$ represents —CONH—, $X^1$ typically represents CH. Where $B^1$ represents —CO—, $X^1$ typically represents N.

In one embodiment, $B^2$ represents —CONH—. In another embodiment, $B^2$ represents —CO—. Where $B^2$ represents —CONH—, $X^2$ typically represents CH. Where $B^2$ represents —CO—, $X^2$ typically represents N.

In one embodiment, $B^3$ represents —CONH—. In another embodiment, $B^3$ represents —CO—. Where $B^3$ represents —CONH—, $X^3$ typically represents CH. Where $B^3$ represents —CO—, $X^3$ typically represents N.

Suitably, $B^1$ and $B^2$ are identical.

In a preferred embodiment, $V^1$ represents a covalent bond. In another embodiment, $V^1$ represents —(CH$_2$)$_v$— in which v is as defined above.

In a preferred embodiment, $V^2$ represents a covalent bond. In another embodiment, $V^2$ represents —(CH$_2$)$_v$— in which v is as defined above.

In a preferred embodiment, $V^3$ represents a covalent bond. In another embodiment, $V^3$ represents —(CH$_2$)$_v$— in which v is as defined above.

Suitably, $V^1$ and $V^2$ are identical.

In one embodiment, $W^1$ represents a covalent bond. In another embodiment, $W^1$ represents —(CH$_2$)$_w$— in which w is as defined above.

In one embodiment, $W^2$ represents a covalent bond. In another embodiment, $W^2$ represents —(CH$_2$)$_2$— in which w is as defined above.

Suitably, $W^1$ and $W^2$ are identical.

Suitably, $Y^1$ and $Y^2$ are identical.

The spacer groups $L^1$, $L^2$ and $L^3$ will suitably comprise any moiety familiar to the person skilled in the art which is capable of forming a bridge between the alkylene chain $Y^1$, $Y^2$ and (where present) $Y^3$ and the residue $Z^1$, $Z^2$ and (where present) $Z^3$ respectively. For example, where $Z^1$ and/or $Z^2$ and/or $Z^3$ is the residue of a polypeptide molecule (e.g. an antibody or a fragment thereof) containing a cysteine residue the corresponding spacer group $L^1$ and/or $L^2$ and/or $L^3$ will suitably be a maleimide residue, which may be covalently linked to the cysteine-containing polypeptide residue $Z^1$ and/or $Z^2$ and/or $Z^3$ via a thiol linkage and to the alkylene chain $Y^1$ and/or $Y^2$ and/or $Y^3$ through the maleimide nitrogen atom.

Suitably, $L^1$ and $L^2$ are identical.

In one embodiment, $M^1$ represents a covalent bond. In another embodiment, $M^1$ represents —(CH$_2$)$_m$— in which m is as defined above.

In one embodiment, $M^2$ represents a covalent bond. In another embodiment, $M^2$ represents —(CH$_2$)$_m$— in which m is as defined above.

In a preferred embodiment, $R^1$ is hydrogen. In another embodiment, $R^1$ represents $C_{1-4}$ alkyl, especially methyl.

In a preferred embodiment, $R^2$ is hydrogen. In another embodiment, $R^2$ represents $C_{1-4}$ alkyl, especially methyl.

Suitably, n is zero or 1.

In a preferred embodiment, n is zero, in which case $M^1$ is directly attached to $X^2$. In another embodiment, n is 1. In a further embodiment, n is 2.

In a preferred embodiment, w is 1. In another embodiment, w is 2. In an additional embodiment, w is 3. In a further embodiment, w is 4. Favourably, w is 1 or 2.

In one embodiment, y is 1. In another embodiment, y is 2. In an additional embodiment, y is 3. In a further embodiment, y is 4. In a still further embodiment, y is 5. In a yet further embodiment, y is 6. Favourably, y is 2, 3 or 4, typically 2 or 4.

In one embodiment, m is 1. In another embodiment, m is 2. In an additional embodiment, m is 3. Favourably, m is 2.

In another aspect, the present invention provides novel scaffold molecules which are valuable intermediates for the attachment of the biologically active moieties of which $Z^1$, $Z^2$ and $Z^3$ are residues. Thus, the invention also provides a compound of formula (II):

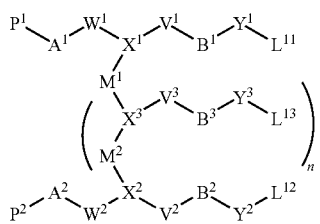
(II)

wherein $L^{11}$, $L^{12}$ and $L^{13}$ represent groups capable of attaching the residue $Z^1$, $Z^2$ and $Z^3$ respectively, or capable of being converted into such groups; and each of the other variables is as defined above in relation to formula (I).

Where $Z^1$ and/or $Z^2$ and/or $Z^3$ is the residue of a polypeptide molecule (e.g. an antibody or a fragment thereof), the corresponding group $L^1$ and/or $L^2$ and/or $L^3$ may be attached to the polypeptide through any available amino acid side-chain or terminal amino acid functional group located in the antibody fragment, for example any free amino, imino, thiol, hydroxy or carboxyl group. Such amino acids may occur naturally in, for example, the antibody fragment or may be engineered into the fragment using recombinant DNA methods (see, for example, U.S. Pat. No. 5,219,996). In a preferred aspect of the invention the two groups are covalently linked through a thiol group of a cysteine residue located in the fragment. The covalent linkage will generally be a disulphide bond or a sulphur-carbon bond, preferably the latter. In one example where a thiol group is used as the point of attachment appropriately activated groups, for example thiol-selective derivatives such as maleimide and cysteine derivatives, may be used.

In a preferred feature, the groups $L^{11}$, $L^{12}$ and (where present) $L^{13}$ are identical and represent maleimide derivatives attached to the remainder of the molecule through the maleimide nitrogen atom. Accordingly, one illustrative subset of the compounds of formula (II) above is represented by the compounds of formula (III):

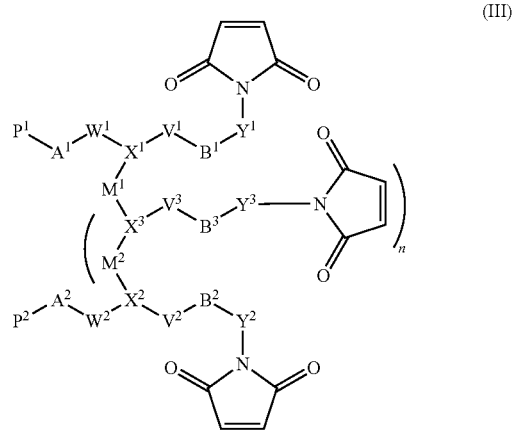
(III)

wherein each of the variables is as defined above in relation to formula (I).

According to a further aspect of the invention there is provided a pharmaceutical composition which comprises a compound of formula (I) as defined above in association with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) may be prepared by a process which comprises attachment of the residues $Z^1$, $Z^2$ and (where present) $Z^3$ to the appropriate compound of formula (II). This process may be accomplished using procedures which are well known to the person skilled in the art such as, for example, the methods described in U.S. Pat. No. 6,251,382 B1, with particular reference to column 23, lines 1 to 50, the contents of which are herein incorporated by reference.

The compounds of formula (II) wherein $P^1$ and $P^2$ are identical and $A^1$ and $A^2$ are both —CONH— may be prepared by a process which comprises reacting a compound of formula (IV) with a compound of formula (V):

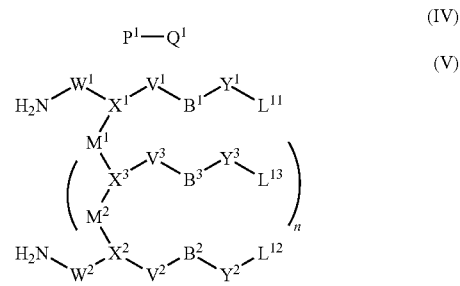

wherein $Q^1$ represents an activated carboxylate moiety; and the remaining variables are as defined above.

Examples of activated carboxylate moieties for the substituent $Q^1$ include acid chlorides; acid anhydrides; and the ester formed when a carboxylic acid ($Q^1$=—$CO_2H$) is reacted with N-hydroxysuccinimide.

The reaction between compounds (IV) and (V) is conveniently effected in a suitable solvent, e.g. dichloromethane, typically in the presence of an organic base, e.g. triethylamine.

The compounds of formula (II) wherein $P^1$ and $P^2$ are identical and $A^1$ and $A^2$ are both —OC(O)N(H)— may be prepared by a process which comprises reacting a compound of formula $P^1$—OC(O)$R^x$, wherein $R^x$ represents a readily displaceable group such as a halogen atom (e.g. chloro), 4-nitrophenoxy or 1-succinimidyloxy; with a compound of formula (V) as defined above.

The requisite intermediate of formula $P^1$—OC(O)$R^x$ may be prepared by treating a compound of formula $P^1$—OH with, for example, phosgene, 4-nitrophenyl chloroformate or N,N'-disuccinimidyl carbonate.

By way of illustration, the compounds of formula (V) wherein n is zero, $B^1$ and $B^2$ are both —CONH—, $Y^1$ and $Y^2$ are identical and $L^{11}$ and $L^{12}$ are identical may be prepared by a process which comprises reacting a compound of formula (VI) with a compound of formula (VII):

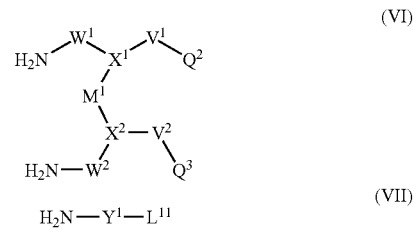

wherein $Q^2$ and $Q^3$ independently represent an activated carboxylate moiety as defined above for $Q^1$; and the remaining variables are as defined above.

The reaction between compounds (VI) and (VII) is conveniently effected in a suitable solvent, e.g. dichloromethane, typically in the presence of an organic base, e.g. triethylamine.

In an alternative procedure, and by way of illustration, the compounds of formula (II) wherein n is zero, $X^1$ and $X^2$ are both N, $B^1$ and $B^2$ are both —CO—, $V^1$ and $V^2$ are both covalent bonds, $Y^1$ and $Y^2$ are identical and $L^{11}$ and $L^{12}$ are identical may be prepared by a process which comprises reacting a compound of formula (VIII) with a compound of formula (IX):

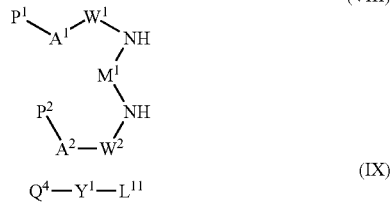

(VIII)

(IX)

wherein $Q^4$ represents an activated carboxylate moiety as defined above for $Q^1$; and the remaining variables are as defined above.

The reaction between compounds (VIII) and (IX) is conveniently effected in a suitable solvent, e.g. dichloromethane, typically in the presence of an organic base, e.g. triethylamine.

The compounds of formula (VIII) wherein $P^1$ and $P^2$ are identical and $A^1$ and $A^2$ are both —NHCO— may be prepared by reacting a compound of formula (X) with a compound of formula (XI):

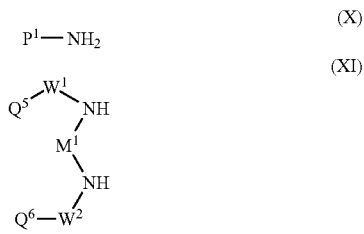

(X)

(XI)

wherein $Q^5$ and $Q^6$ independently represent an activated carboxylate moiety as defined above for $Q^1$; and the remaining variables are as defined above.

The reaction between compounds (X) and (XI) is conveniently effected in a suitable solvent, e.g. dichloromethane, typically in the presence of an organic base, e.g. triethylamine.

The compounds of formula (II) wherein $P^1$ and $P^2$ are identical and $A^1$ and $A^2$ are both —N(H)C(O)O— may be prepared by a process which comprises reacting a compound of formula (X) as defined above with a compound of formula (XII):

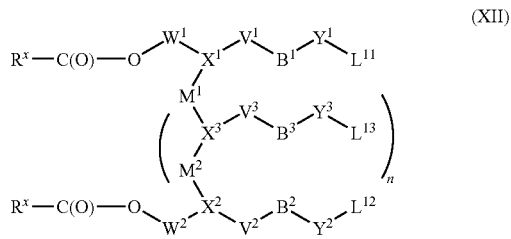

(XII)

wherein $R^x$ and the remaining variables are all as defined above.

The intermediates of formula (XII) may be prepared by treating a compound of formula (XIII):

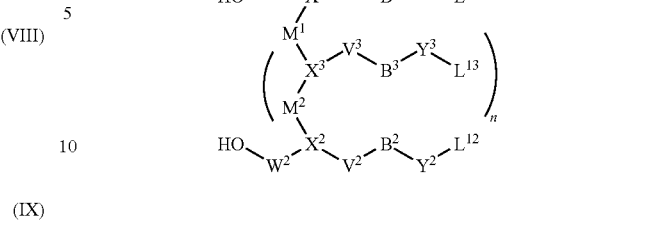

(XIII)

wherein the variables are all as defined above; with, for example, phosgene, 4-nitrophenyl chloroformate or N,N'-disuccinimidyl carbonate.

Where $R^2$ is $C_{1-4}$ alkyl, attachment of the $R^2$ moiety may be effected by conventional N-alkylation procedures.

The compounds of formula (II) wherein $P^1$ and $P^2$ are identical and $A^1$ and $A^2$ are both —NHCONH— may be prepared by a process which comprises reacting a compound of formula $P^1$—N=C=O with a compound of formula (V) as defined above.

The requisite intermediate of formula $P^1$—N=C=O may, for example, be prepared by treating a compound of formula (X) as defined above with phosgene.

Where they are not commercially available, the compounds of formula (IV), (VI), (VII), (IX), (X), (XI) and (XIII) may be prepared by methods analogous to those described in the accompanying Examples, or by standard methods well known from the art.

Where a mixture of products is obtained from any of the processes described above for the preparation of compounds according to the invention, the desired product can be separated therefrom at an appropriate stage by conventional methods such as gel permeation chromatography; cation or anion exchange; preparative HPLC; or column chromatography utilising, for example, silica and/or alumina in conjunction with an appropriate solvent system.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The following non-limiting Examples illustrate the invention.

INTERMEDIATE 1

(4-Maleimidyl-butyl)-carbamic acid tert-butyl ester

To a solution of N-BOC-1,4-diaminobutane (8.324 g, 0.044 mol) in dry toluene (50 ml) was added maleic anhydride (4.336 g, 0.044 mol) and the solution heated at reflux under Dean-Stark conditions for two days. The solvent was removed and the residue purified by silica column chromatography eluting with 25-40% ethyl acetate in hexane to give the title compound, 1.461 g, 12%, as a white solid.

m/z (LCMS ES+, 70V) 291 (MH+).

$\delta$H (CDCl$_3$) 6.63 (2H, s), 4.46 (1H, br), 3.48 (2H, t, J7.1 Hz), 3.08 (2H, m), 1.56 (2H, p, J7.4 Hz), 1.41 (2H, m), 1.38 (9H, s).

INTERMEDIATE 2 meso-2,3-Bis-tert-butoxycarbonylamino-succinic acid

To a solution of meso-2,3-diamino succinic acid (1.96 g, 0.013 mol) and triethylamine (5.36 g, 0.053 mol) in water (50 ml) was added a solution of di-tert-butyl dicarbonate (6.35 g, 0.029 mol) in dioxane (30 ml) over a period of 20 min. After 2 hours the solvent was reduced to 10 ml, diluted with water to 50 ml and washed with dichloromethane (4×30 ml). The solution was then acidified to pH 1-2 with 2M HCl and extracted into ethyl acetate (5×50 ml). The ethyl acetate solution was dried over magnesium sulphate and the solvent removed to yield the title compound, 4.345 g, 94%, as a colourless glass.

m/z (LCMS ES+, 70V) 371 (MNa$^+$).

$\delta$H (d6-DMSO, 370K) 6.03 (2H, br), 4.49 (2H, s), 1.42 (18H, s).

INTERMEDIATE 3

{tert-Butoxycarbonyl-[2-(tert-butoxycarbonyl-carboxymethyl-amino)-ethyl]-amino}-acetic acid To a stirred suspension of ethylenediamine-N,N'-diacetic acid (1.00 g, 5.68 mmol) in methanol (150 ml) was added triethylamine (2.30 g, 22.7 mmol) followed by di-tert-butyl dicarbonate (2.48 g, 11.4 mmol). The suspension was heated at reflux for 10 minutes until the majority of solids had dissolved then allowed to cool to ambient temperature and stirred for 2 h. The suspension was filtered, the solvent removed, the residue dissolved in water (40 ml) and the pH raised to approximately 8-9 with triethylamine. The solution was washed with dichloromethane (5×40 ml), acidified with 1M HCl to a pH of approximately 1 and extracted with DCM (10×40 ml) followed by ethyl acetate (10×40 ml). The ethyl acetate and dichloromethane fractions were dried over magnesium sulphate, combined and the solvent removed to yield the desired material, 1.558 g, 74%, as a white solid.

m/z (LCMS ES+, 70V) 399 (MNa$^+$).

$\delta$H (d6-DMSO, 380K) 3.86 (4H, s), 3.37 (4H, s), 1.42 (18H, s).

INTERMEDIATE 4

3-(tert-Butoxycarbonyl-{2-[tert-butoxycarbonyl-(2-carboxy-ethyl)-amino]-ethyl}-amino)-propionic acid To ethylene diamine-N,N'-dipropionic acid di-hydrochloride salt (2.00 g, 7.21 mmol) in water (50 ml) and triethylamine (4.38 g, 43 mmol) was added di-tert butyl di-carbonate (3.307 g, 15 mmol) in dioxane (30 ml) over a period of 10 minutes. The reaction was left overnight at ambient temperature, the dioxane removed under reduced pressure and the remaining aqueous solution washed with dichloromethane (4×50 ml). The aqueous layer was acidified with concentrated HCl to a pH of approximately 1, and the resulting white precipitate extracted into ethyl acetate (5×60 ml). The ethyl acetate solution was dried over magnesium sulphate and the solvent removed to yield the product, 2.68 g, 92%, as a white solid.

m/z (LCMS ES+, 70V) 472 (MNa$^+$).

$\delta$H (d6-DMSO, 380K) 3.41 (4H, t, J7.2 Hz), 3.31 (4H, s), 2.46 (4H, t, J7.2 Hz) 1.44 (18H, s).

INTERMEDIATE 5

2,3-Bis-tert-butoxycarbonylamino-succinic acid bis-succinimidyl ester

To Intermediate 2 (1.500 g, 4.3 mmol) in dichloromethane (20 ml) were added N-hydroxy succinimide (1.240 g, 10.78 mmol) and EDC (2.066 g, 10.78 mmol). After overnight reaction the solution was diluted to 50 ml with dichloromethane, washed with water (3×30 ml), dried over magnesium sulphate and the solvent removed to give a white solid residue. The residue was purified by silica column chromatography eluting with 50-65% ethyl acetate in hexane to yield the desired di-NHS ester, 277 mg, 12%, as a white solid.

m/z (LCMS ES+, 70V) 565 (MNa$^+$).

$\delta$H (CDCl$_3$-rotamers) 6.47, 6.17, 6.10 (2H, 3xbr), 5.35, 5.25, 5.10 (2H, 3xbr), 2.82 (8H, s), 1.44, 1.42 (18H, 2xs).

INTERMEDIATE 6

{tert-Butoxycarbonyl-[2-(tert-butoxycarbonyl-carboxymethyl-amino)-ethyl]-amino}-acetic acid bis-succinimidyl ester To a suspension of Intermediate 3 (200 mg, 0.53 mmol) in dichloromethane (4 ml) was added triethylamine (269 mg, 2.66 mmol) and once a clear solution was obtained, N-hydroxy succinimide (153 mg, 1.33 mmol) followed by EDC (255 mg, 1.33 mmol) were added. LCMS of the reaction at 45 min and 5 h showed it to have stopped before completion. An extra 1.5 equivalents of both N-hydroxy succinimide and EDC were added in DCM (3 ml) and the reaction left overnight during which time a poorly soluble white solid formed. The reaction mix was diluted to 40 ml with dichloromethane, the solution/suspension washed with 0.1M HCl (6×50 ml), dried over magnesium sulphate and the solvent removed. The resulting white solid residue was purified by silica column chromatography eluting with 70% ethyl acetate in hexane to yield the desired di-NHS ester, 38 mg, 13%, as a poorly soluble white solid.

m/z (LCMS ES+, 70V) 593 (MNa$^+$).

$\delta$H (d6-DMSO, 380K) 4.36 (4H, s), 3.46 (4H, s), 2.84 (8H, s), 1.45 (18H, s).

INTERMEDIATE 7

3-(tert-Butoxycarbonyl-{2-[tert-butoxycarbonyl-(2-carboxy-ethyl)-amino]-ethyl}-amino)-propionic acid bis succinimidyl ester To Intermediate 4 (1.00 g, 2.48 mmol) in dichloromethane (40 ml) were added triethylamine (751 mg, 7.43 mmol), N-hydroxy succinimide (712 mg, 6.19 mmol) and EDC (1.186 g, 6.19 mmol). After 2 h 20 min a further 474 mg of EDC was added and the reaction left overnight at ambient temperature. The solvent was removed and the residue purified by silica column chromatography, eluting 70% ethyl acetate in hexane to yield the product, 773 mg, 52%, as a white solid.

m/z (LCMS ES+, 70V) 621 (MNa$^+$).

$\delta$H (d6-DMSO, 380K) 3.54 (4H, t, J7.0 Hz), 3.37 (4H, s), 2.91 (4H, t, J7.0 Hz), 2.83 (8H, s), 1.46 (18H, s).

INTERMEDIATE 8

2,3-Bis-tert-butoxycarbonylamino-N,N'-bis-(4-maleimidyl-butyl)-succinamide

To Intermediate 1 (300 mg, 1.120 mmol) was added 1:1 trifluoroacetic acid:dichloromethane (8 ml). After 30 minutes the solvent was removed, the residue dissolved in dichloromethane and Intermediate 5 (276 mg, 0.509 mmol) added, followed immediately by triethylamine (258 mg, 2.546 mmol). After 30 minutes PS-TsCl scavenger resin (0.5 g, 1.44 mmol/g) was added, stirred for 1 hour and filtered off. The solvent was removed and the residue purified by silica column chromatography eluting with 75-100% ethyl acetate in hexane to give the desired material, 115 mg, 35%, as a white solid.

m/z (LCMS ES+, 70V) 649 (MH+).

$\delta$H (CDCl$_3$) 6.64 (2H, br), 6.62 (4H, s), 6.28 (2H, br), 4.30 (2H, br), 3.46 (4H, t, J6.9 Hz), 3.17 (4H, m), 1.57-1.40 (8H, m), 1.39 (18H, s).

INTERMEDIATE 9

(2-{tert-Butoxycarbonyl-[(2-(methoxy-polyethoxy)-ethylcarbamoyl)-methyl]-amino}-ethyl)-[(2-(methoxy-polyethoxy)-ethylcarbamoyl)-methyl]-carbamic acid tert-butyl ester To a solution of Intermediate 6 (5.7 mg, 0.010 mmol) in dichloromethane (5 ml) were added 20K methoxy-PEG-amine (500 mg, 0.025 mmol) (purchased from Rapp Polymere) and triethylamine (5.1 mg, 0.050 mmol). The reaction was left overnight, diluted with dichloromethane to 25 ml and stirred for 3 days with MP-Tosic acid scavenger resin (3.0 g, 1.43 mmol/g). The resin was filtered off, the solution diluted to 50 ml with dichloromethane and washed with 0.1M HCl (4×30 ml). The solution was dried over magnesium sulphate and the solvent removed to give the 40K product, 370 mg, 92%, as a waxy white solid.

$\delta$H (CDCl$_3$) 4.1-3.3 (~3600H, brm), 3.30 (6H, s), 1.42 (18H, br).

INTERMEDIATE 10

(2-{tert-Butoxycarbonyl-[2-(2-(methoxy-polyethoxy)-ethylcarbamoyl)-ethyl]-amino}-ethyl)-[2-(2-(methoxy-polyethoxy)-ethylcarbamoyl)-ethyl]-carbamic acid tert-butyl ester To a solution of Intermediate 7 (11.1 mg, 0.019 mmol) in dichloromethane (10 ml) were added 20K methoxy-PEG-amine (1.00 g, 0.05 mmol) (purchased from Rapp Polymere) and triethylamine (9.4 mg, 0.093 mmol). The reaction was left overnight, diluted with dichloromethane to 50 ml and stirred for 3 days with MP-Tosic acid scavenger resin (6.0 g, 1.43 mmol/g). The resin was filtered off, the solution washed with 0.1M HCl (4×50 ml), dried over magnesium sulphate and the solvent removed to quantitatively yield the 40K product as a waxy white solid.

$\delta$H (CDCl$_3$) 4.5-3.0 (~3600H, brm), 3.30 (6H, s), 2.4 (4H, br),1.37 (18H, brs).

INTERMEDIATE 11

2,3-Diamino-N,N'-bis-[4-maleimidyl-butyl]-succinamide bis TFA salt

Intermediate 8 (4.0 mg, 0.0062 mmol) was dissolved in dichloromethane (1 ml) and trifluoroacetic acid (1 ml) added. After half an hour the solvent was removed and the residue used crude in the synthesis of Example 1.

m/z (LCMS ES+, 70V) 449 (MH+).

$\delta$H (d6-DMSO) 6.93 (4H, s), 4.14 (2H, s), 3.32 (4H, t, J6.8 Hz), 3.06, 2.96 (4H, 2xm), 1.42 (4H, m), 1.29 (4H, m).

INTERMEDIATE 12

N-(2-(Methoxy-polyethoxy)-ethyl)-2-(2-{[(2-(methoxy-polyethoxy)-ethylcarbamoyl)-methyl]-amino}-ethylamino)-acetamide di-hydrochloride Intermediate 9 (approx 400 mg) was dissolved in dichloromethane (4 ml), and trifluoroacetic acid (4 ml) added. After half an hour the solvent was removed, the residue dissolved in dichloromethane (100 ml), washed with 0.1M HCl (3×100 ml), dried over magnesium sulphate and the solvent removed to yield the salt (386 mg) as an off-white solid.

$\delta$H (CDCl$_3$) 4.2-3.0 (~3600H, brm), 3.31 (6H, s).

INTERMEDIATE 13

N-(2-(Methoxy-polyethoxy)-ethyl)-3-{2-[2-(2-(methoxy-polyethoxy)-ethylcarbamoyl)-ethylamino]-ethylamino}-propionamide di hydrochloride salt Intermediate 10 (460 mg) was dissolved in dichloromethane (5 ml), and trifluoroacetic acid (5 ml) added. After half an hour the solvent was removed, the residue dissolved in dichloromethane (60 ml), washed with 0.1M HCl (4×60 ml), dried over magnesium sulphate and the solvent removed to yield the salt (460 mg) as a white solid.

$\delta$H (CDCl$_3$) 7.20 (2H, br), 4.0-3.0 (~3600H, brm), 3.31 (6H, s), (remaining signals obscured by broad H$_2$O signal).

EXAMPLE 1

N,N'-Bis-[4-maleimidylbutyl]-2,3-bis-(3-(methoxy-polyethoxy)-propionylamino)-succinamide To Intermediate 11 (4.0 mg, 6.2 micromol) in dichloromethane (8 ml) were added M-PEG-SPA from Nektar (formerly Shearwater) (393 mg, MW22K) followed by triethylamine (13 mg, 123 μmol). The reaction was stirred at ambient temperature for 3 days followed by 2 days at gentle reflux. To the reaction was added MP-TsCl resin (0.25 g, 1.44 mmol/g), the reaction gently stirred for 2 hours and the resin filtered off. The reaction was diluted to 50 ml with dichloromethane, washed with 0.1M HCl (3×30 ml), dried over magnesium sulphate and the solvent removed. $^1$H NMR showed the presence of unreacted M-PEG-SPA so the residue was dissolved in distilled water (10 ml) and left overnight to hydrolyse the ester. The aqueous solution was washed with diethyl ether (2×50 ml), extracted into dichloromethane (5×50 ml), dried over magnesium sulphate and the solvent removed to yield a white solid containing a mixture of mPEG-propionic acid, the mono-PEGylated species and the desired di-PEGylated species.

$\delta$H (CDCl$_3$) 7.95 (2H, br), 7.55 (2H, br), 6.63 (4H, s), 4.89 (2H, br), 4.1-3.0 (~4000H, brm), 2.52 (4H, t), 1.58 (4H, m), 1.38 (4H, m).

EXAMPLE 2

3-Maleimidyl-N-(2-{[3-maleimidyl-propionyl]-[(2-(methoxy-polyethoxy)-ethylcarbamoyl)-methyl]-amino}-ethyl)-N-[(2-(methoxy-polyethoxy)-ethyl-carbamoyl)-methyl]-propionamide Intermediate 12 (386 mg, 0.0097 mmol) was dissolved in dichloromethane (7 ml) and to it added maleimido propionic acid N-hydroxysuccinimide ester (6.4 mg, 0.024 mmol) followed by triethylamine (39 mg, 0.386 mmol). After overnight reaction the solvent was removed, the residue dissolved in dichloromethane (6 ml and half dropped into rapidly stirring diethyl ether (80 ml) to give a white precipitate. This was filtered off under an atmosphere of nitrogen, dissolved in dichloromethane and the solvent removed to give a material with only partial maleimide addition. An 80 mg batch of this material was retreated with 10 equivalents of maleimido propionic acid N-hydroxysuccinimide ester and 40 equivalents of triethylamine in dichloromethane (2 ml) for 3 days, giving, after precipitation from diethyl ether, 80 mg of a substantially unchanged product. This material was then treated with 10 equivalents of maleimido propionyl chloride (from maleimido propionic acid treated with 1:1 oxalyl chloride:dichloromethane (4 ml) for 3 hours at ambient temperature) and 40 equivalents of triethylamine, giving, after precipitation from diethyl ether, material determined by $^1$H NMR to consist of roughly a 1:1 mixture of the desired di-maleimide and the mono-maleimide species.

$\delta$H (CDCl$_3$) 6.65 (4H, m), 4.2-3.2 (~3600H, brm), 3.31 (6H, s), 2.57 (4H, m).

EXAMPLE 3

3-Maleimidyl-N-(2-{[3-(maleimidyl)-propionyl]-[2-(2-(methoxy-polyethoxy)-ethylcarbamoyl)-ethyl]-amino}-ethyl)-N-[2-(2-(methoxy-polyethoxy)-ethyl-carbamoyl)-ethyl]-propionamide To maleimido propionic acid in dichloromethane (2 ml) was added oxalyl chloride (2 ml) and after 4.5 hours the solvent thoroughly removed under reduced-pressure. To this crude acid chloride was added Intermediate 13 (116 mg, 2.9 µmol) in dichloromethane (2 ml) followed by triethylamine (12 mg, 116 µmol). After three days the solvent was removed, the residue redissolved in dichloromethane (3 ml) and added slowly to rapidly stirred diethyl ether (100 ml). The resulting white precipitate was filtered off, washed with diethyl ether, redissolved in dichloromethane and filtered. The solvent was then removed to yield the product in quantitative yield as a white, waxy solid.

$\delta$H (CDCl$_3$) 6.81 (1H, t), 6.78 (1H, t), 6.69,6.68 (4H, 2xs), 4.0-3.2 (~3600H, brm), 3.35 (6H, s), 2.72 (4H, m), (remaining signals obscured by broad H$_2$O signal).

EXAMPLE 4

DiFab' Conjugate of Example 1 Product 5 ml of an engineered Fab' containing a single hinge thiol (see for example U.S. Pat. No. 5,677,425; WO 98/25971), at 20 mg/ml in 0.1M phosphate, 2 mM EDTA, pH6, was reduced with a 20-fold molar excess of 2-mercaptoethylamine for 1 hour at ambient temperature. The reductant was then removed by gel filtration on five PD10 columns in parallel equilibrated in 0.1M phosphate, 2 mM EDTA, pH6. The concentration of the pooled reduced Fab' was determined by A280 (11.8 mg/ml) and then 40 mg of reduced Fab' was conjugated to 20 mg of Example 1 (stock solution at 50 mg/ml in 0.1M phosphate, 2 mM EDTA, pH6) for 16 hours at ambient temperature. The extent of conjugation was assessed by SDS-PAGE and size-exclusion HPLC. To 3.33 ml of the Fab':PEG conjugation reaction was added 6.67 ml of distilled water and 100 µl of 1M acetic acid, and 10 ml of this was loaded onto a 4 ml SP-Sepharose HP C10 column (GE Healthcare) equilibrated in 50 mM acetate, pH4.5, at 2 ml/min. The column was eluted with a 16 ml linear gradient of 0-250 mM NaCl in 50 mM acetate, pH4.5. 2 ml fractions were collected and those containing PEG-DiFab' as assessed by SDS-PAGE were pooled. The pooled fractions were concentrated with 10000 MWCO spin cartridges to 310 µl. 300 µl of this was loaded onto a Superose 6 HR10/30 gel filtration column (GE Healthcare) equilibrated in 50 mM acetate, 125 mM NaCl, pH5.5, at 0.5 ml/min. The Superose 6 column was eluted with an isocratic gradient of 50 mM acetate, 125 mM NaCl, pH5.5, at 0.5 ml/min. 0.5 ml fractions were collected and those containing only PEG-DiFab' (#B7-B5) as assessed by SDS-PAGE were pooled. The pooled fractions were concentrated with 10000 MWCO spin cartridges to 100 µl. The concentration of the PEG-DiFab' was determined by A280 and the purity was assessed by reducing and non-reducing SDS-PAGE.

EXAMPLE 5

DiFab' Conjugate of Example 2 Product 4 ml of an engineered Fab' containing a single hinge thiol (see for example U.S. Pat. No. 5,677,425; WO 98/25971) at 20 mg/ml in 0.1M phosphate, 2 mM EDTA, pH6, was reduced with a 20-fold molar excess of 2-mercaptoethylamine for 1 hour at ambient temperature. The reductant was then removed by gel filtration on four PD10 columns in parallel equilibrated in 0.1M phosphate, 2 mM EDTA, pH6. The concentration of the pooled reduced Fab' was determined by A280 (12.0 mg/ml) and then 22.77 mg of reduced Fab' was conjugated to 4.8 mg of Example 2 for 16 hours at ambient temperature. The extent of conjugation was assessed by reducing and non-reducing SDS-PAGE and size-exclusion HPLC. Conjugate purification and analysis as for Example 4.

EXAMPLE 6

DiFab' Conjugate of Example 3 Product 4 ml of an engineered Fab' containing a single hinge thiol (see for example U.S. Pat. No. 5,677,425; WO 98/25971) at 20 mg/ml in 0.1M phosphate, 2 mM EDTA, pH6, was reduced with a 20-fold molar excess of 2-mercaptoethylamine for 1 hour at ambient temperature. The reductant was then removed by gel filtration on four PD10 columns in parallel equilibrated in 0.1M phosphate, 2 mM EDTA, pH6. The concentration of the pooled reduced Fab' was determined by A280 (14.6 mg/ml) and then in duplicate 14.2 mg of reduced Fab' was conjugated to 4 mg of Example 3 (stock solution at 20 mg/ml in distilled water) for 16 hours at ambient temperature. The extent of conjugation was assessed by SDS-PAGE and size-exclusion HPLC. The duplicate Fab':PEG conjugation reactions were pooled and to them was added 7.56 ml of distilled water and 100 µl of 1M acetic acid.

9.7 ml of this was loaded onto a 4 ml SP-Sepharose HP C10 column (GE Healthcare) equilibrated in 50 mM acetate, pH4.5, at 2 ml/min. The column was eluted with a 16 ml linear gradient of 0-250 mM NaCl in 50 mM acetate, pH4.5. 2 ml fractions were collected and those containing PEG-DiFab' as assessed by SDS-PAGE were pooled. The pooled fractions were concentrated with 10000 MWCO spin cartridges to 260 µl. 200 µl of this was loaded onto a Superose 6 HR10/30 gel filtration column (GE Healthcare) equilibrated in 50 mM acetate, 125 mM NaCl, pH5.5, at 0.5 ml/min. The Superose 6 column was eluted with an isocratic gradient of 50 mM acetate, 125 mM NaCl, pH5.5 at 0.5 ml/min. 0.5 ml fractions were collected and those containing only PEG-DiFab' as assessed by SDS-PAGE were pooled. The pooled fractions were concentrated with 10000 MWCO spin cartridges to 570 µl. The concentration of the PEG-DiFab' was determined by A280 (3.5 mg/ml) and the purity was assessed by reducing and non-reducing SDS-PAGE, endotoxin assay and size-exclusion HPLC.

The invention claimed is:

1. A compound of the following formula:

$$P^1-A^1-W^1-X^1(-M^1-)-V^1-B^1-Y^1-L^1-Z^1$$
$$P^2-A^2-W^2-X^2-V^2-B^2-Y^2-L^2-Z^2$$
(I)

wherein
  $P^1$ and $P^2$ independently represent a polyethylene glycol (PEG) moiety;
  $Z^1$ and $Z^2$ independently represent a polyclonal, monoclonal, multi-valent, multi-specific, humanized or chimeric antibody, a single chain antibody, a Fab fragment, a Fab' or F(ab')$_2$ fragment, or an epitope-binding fragment thereof;
  $X^1$ and $X^2$ independently represent N;
  $A^1$ and $A^2$ independently represent —NHCO—;
  $B^1$ and $B^2$ independently represent —CO—;
  $V^1$ and $V^2$ independently represent a covalent bond;
  $W^1$ and $W^2$ independently represent —(CH$_2$)$_w$—;
  $Y^1$ and $Y^2$ independently represent —(CH$_2$)$_y$—;
  $L^1$ and $L^2$ independently represent a maleimide moiety, each of which is covalently linked to $Z^1$ and $Z^2$, respectively, and each of which is covalently linked through the maleimide nitrogen atom to $Y^1$ and $Y^2$, respectively;
  $M^1$ represents —(CH$_2$)$_m$—;
  w is 1 or 2;
  y is 1, 2, 3, 4, 5 or 6; and
  m is 2.

2. A compound as claimed in claim 1 that is
  DiFab'-conjugated 3-maleimidyl-N-(2-{[3-maleimidyl-propionyl]-[(2-(methoxy-polyethoxy)-ethylcarbamoyl)-methyl]-amino}-ethyl)-N-[(2-(methoxy-polyethoxy)-ethylcarbamoyl)-methyl]-propionamide; or
  DiFab'-conjugated 3-maleimidyl-N-(2-{[3-(maleimidyl)-propionyl]-[2-(2-(methoxy-polyethoxy)-ethylcarbamoyl)-ethyl]-amino}-ethyl)-N-[2-(2-(methoxy-polyethoxy)-ethylcarbamoyl)-ethyl]-propionamide.

3. A compound of the following formula:

$$P^1-A^1-W^1-X^1(-M^1-)-V^1-B^1-Y^1-\text{maleimide}$$
$$P^2-A^2-W^2-X^2-V^2-B^2-Y^2-\text{maleimide}$$

wherein
  $P^1$ and $P^2$ independently represent a polyethylene glycol (PEG) moiety;
  $X^1$ and $X^2$ independently represent N;
  $A^1$ and $A^2$ independently represent —NHCO—;
  $B^1$ and $B^2$ independently represent —CO—;
  $V^1$ and $V^2$ independently represent a covalent bond;
  $W^1$ and $W^2$ independently represent —(CH$_2$)$_w$—;
  $Y^1$ and $Y^2$ independently represent —(CH$_2$)$_y$—;
  $M^1$ represents —(CH$_2$)$_m$—;
  w is 1 or 2;
  y is 1, 2, 3, 4, 5 or 6; and
  m is 2.

4. A pharmaceutical composition comprising a compound as claimed in claim 1 in association with one or more pharmaceutically acceptable carriers, excipients or diluents.

5. A pharmaceutical composition comprising a compound as claimed in claim 2 in association with one or more pharmaceutically acceptable carriers, excipients or diluents.

6. A compound as claimed in claim 3 that is 3-Maleimidyl-N-(2-{[3-maleimidyl-propionyl]-[(2-(methoxy-polyethoxy)-ethylcarbamoyl)-methyl]-amino}-ethyl)-N-[(2-(methoxy-polyethoxy)-ethylcarbamoyl)-methyl]-propionamide; or
  3-Maleimidyl-N-(2-{[3-(maleimidyl)-propionyl]-[(2-(methoxy-polyethoxy)-ethylcarbamoyl)-ethyl]-amino}-ethyl)-N-[2-(2-(methoxy-polyethoxy)-ethylcarbamoyl)-ethyl]-propionamide.

* * * * *